United States Patent [19]

Satzinger et al.

[11] 3,966,779

[45] June 29, 1976

[54] THYMOL DERIVATIVES AND A PROCESS FOR THEIR PREPARATION

[75] Inventors: Gerhard Satzinger, Denzlingen; Manfred Franz Herrmann, St. Peter, both of Germany

[73] Assignee: Warner-Lambert Company, Morris Plains, N.J.

[22] Filed: Nov. 29, 1974

[21] Appl. No.: 528,125

Related U.S. Application Data

[63] Continuation-in-part of Ser. No. 356,031, April 30, 1973, abandoned.

[52] U.S. Cl. ............................ 260/404; 260/479 R; 260/463; 424/301; 424/311; 424/312
[51] Int. Cl.² .................. C07C 69/24; C07C 69/26; C07C 69/96
[58] Field of Search ................ 260/463, 479 R, 404

[56] References Cited
UNITED STATES PATENTS

| | | | |
|---|---|---|---|
| 3,226,419 | 12/1965 | Zaugg et al. ........................ | 260/463 |
| 3,341,572 | 9/1967 | Engelhard et al. ............... | 260/479 R |
| 3,454,629 | 7/1969 | Daeniker et al. ................... | 260/519 |
| 3,668,238 | 6/1972 | Clemence .......................... | 260/488 |
| 3,681,437 | 8/1972 | Dedieu et al. ................... | 260/479 R |
| 3,717,611 | 2/1973 | Baumer et al. ............. | 260/45.95 G |

FOREIGN PATENTS OR APPLICATIONS

| | | | |
|---|---|---|---|
| 1,313,297 | 11/1962 | France ................................ | 260/479 |
| 905,738 | 6/1949 | Germany .......................... | 260/479 |
| 37/16725 | 12/1969 | Japan ................................ | 260/463 |
| 745,070 | 2/1956 | United Kingdom ................ | 260/479 |

OTHER PUBLICATIONS

Credner, et al; Arzneimittelforschung, 17 (1967) pp. 305–309.

*Primary Examiner*—Joseph Paul Brust
*Attorney, Agent, or Firm*—Albert H. Graddis; Frank S. Chow; George M. Yahwak

[57] ABSTRACT

The present invention relates to new thymol derivatives with strong sympatholytic effect and low toxicity and to a process for their preparation.

These novel thymol derivatives have the following general formula:

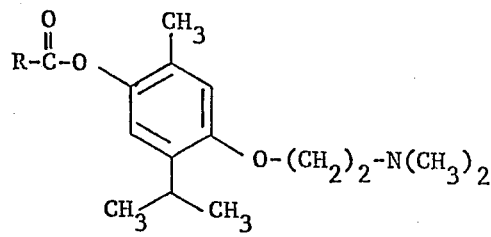

wherein R is an alkyl group of 4 to 11 carbon atoms or an alkoxy group R'—O— wherein R' is an alkyl group of 3 to 10 carbon atoms, and their pharmaceutically acceptable salts.

6 Claims, No Drawings

THYMOL DERIVATIVES AND A PROCESS FOR THEIR PREPARATION

This application is a continuation-in-part of U.S. Application Ser. No. 356,031, filed Apr. 30, 1973, now abandoned.

Of the basically-substituted thymol ethers only [(β-(4-acetoxythymoxy)-ethyl]-dimethylamine, known generally as thymoxamine, has gained acceptance as an agent useful in therapy for disturbed peripheral circulation. There have been attempts to overcome the pharmaceutical disadvantages of this substance, which include low absorbability, short duration of action, relative toxicity and instability (cf., e.g., Arzneimittelforschung 17, 305–309 (1967), but the resulting derivatives obtained by altering the molecular structure were found to have no therapeutic value.

Many prior patents disclose thymol derivatives falling within two broad groups. Group I compounds have the structural formula:

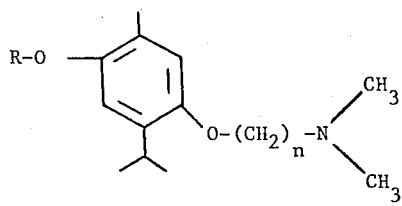

wherein R is acetyl and n is 2 or 3; Group II compounds have the structural formula:

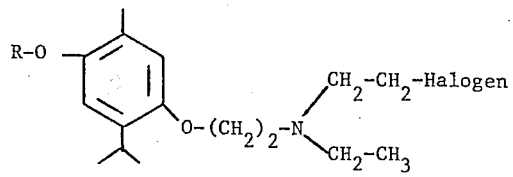

wherein R is acyl with 2 to 6 carbon atoms, and halogen refers to all halogens.

The compounds of Group II represent halogenamine-type substances showing a highly dangerous and N-lost function which is not acceptable from a medical view. This group of compounds, therefore, have little utility and have never been introduced commercially.

The compounds of Group I are known as being relatively unstable, and even though these products show a highly interesting peripheral dilating activity, they suffer from a rather short lasting action due to a certain instability caused by a hydrolytic cleavage of the phenolic ester linkage in vivo. It has, therefore, not been previously possible to prepare parental forms of thymoxamine (Group I).

In an attempt to develop new thymoxamine derivatives suitable for parental preparations and with improved peripheral dilating properties it has now been found that compounds of the general formula I:

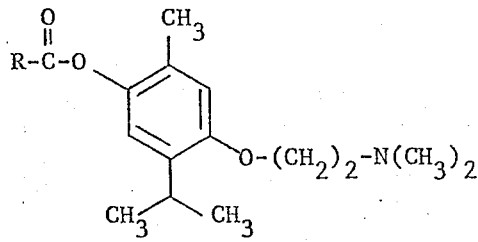

in which R represents an alkyl group of at least 4 to 11 carbon atoms, or an alkoxy group R'—O— wherein R' is an alkyl group of at last 3 to 10 carbon atoms, and their pharmaceutically acceptable salts possess these properties.

Typical compounds of the present invention within formula I are, e.g., [β-(4-isopropoxycarboxythymoxy)-ethyl]-dimethylamine, [β-(4-isovaleryloxythymoxy)-ethyl]-dimethylamine, [β-(4-capryloxythymoxy)-ethyl]-dimethylamine, [β-(4-caprinyloxythymoxy)-ethyl]-dimethylamine, [β-(4-laurinyloxythymoxy)-ethyl]-dimethylamine, [β-(4-isocaprinyloxythymoxy)-ethyl]-dimethylamine, [β-4-capronyloxythymoxy)-ethyl]-dimethylamine and the salts of these compounds.

The compounds of the formula I can be prepared by methods known generally, but somewhat more vigorous conditions have to be used by reason of the appreciable steric hindrance encountered. These conditions, for example, include heating the compound II

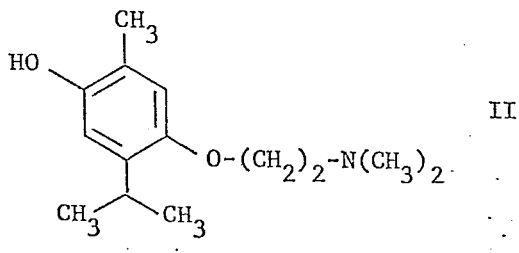

with the anhydride of the corresponding alkancarbonic acid in pyridine or quinoline as the reaction medium to 100° to 170°C, preferably 130° to 150°C, for one to several hours, or by transforming compound II to its alkali metal salt in an ether, preferably in tetrahydrofurane, and in the presence of dimethylformamide or dimethylsulfoxide. The alkali metal salt is then formed by reaction with sodium hydride or an alkali metal alcoholate. The alkali metal salt thus formed is allowed to react in suspension with the chloride of the corresponding alkane or alkoxy carbonic acid at 40° to 80°C for 2 to 6 hours.

When compared to thymoxamine the compounds of the present invention are distinguished by the fact that even in low dosage and by peroral administration they exhibit a typical α-receptor blocking effect as demonstrated by adrenaline inversion tests. Thus these compounds have the desired therapeutic effect on oral application of acting as effective peripheral dilators.

The compound II can be prepared by careful hydrolysis of commercial thymoxamine, or by diazotization and decomposition of the corresponding 4-amino-derivative which is easily obtained by nitration and reduction of thymyl-β-dimethylaminoethylether.

Because of their favorable therapeutic ratio, the new thymol derivatives of the present invention can be used as such or in the form of pharmaceutical preparations with suitable and usual carriers and adjuvants for oral, subcutaneous, intravenous or other application. Suitable forms for administration are tablets, capsules, sugar coated tablets, suspensions and suppositories.

Depending on the indication, the active ingredient in each individual dosage form may be within the range of 2 to 50 mg, preferably about 10 mg.

Correct elementary analysis have been obtained for all of the compounds obtained in the following examples:

EXAMPLE 1

[β-(4-Isovaleryloxythymoxy)-ethyl]-dimethylamine 31 g of Compound II are taken up in 60 ml of pyridine which has been dried over KOH, mixed with 54.2 g of isovaleric acid anhydride and then heated to 140°C for 4 hours. Subsequently, any excess pyridine and anhydride are removed by evaporation under reduced pressure and the residue is taken up in ether, filtered and HCl gas is bubbled through. The crude hydrochloride which precipitates is recrystallized from ethyl acetate-Dioxane. Yield, 43.0 g (82.6% of theory), M.P. 182° – 183°C.

EXAMPLE 2

[β-(4-Capronyloxythymoxy)-ethyl]-dimethylamine 45 g of Compound II together with 85.6 g of capronic acid anhydride and 80 g of pyridine are heated to 130°C for 5 hours. The product formed is isolated as described in Example 1 as the hydrochloride. Yield, 37 g (60% of theory), M.P. 177° – 178°C (from isopropanol).

EXAMPLE 3

[β-(4-Capryloxythymoxy)-ethyl]-dimethylamine

A solution of 17 g of compound II in 90 ml of tetrahydrofuran is added dropwise to a suspension of 4 g of NaH (50%) in 90 ml of dry tetrahydrofuran and 30 ml of dimethylformamide. When hydrogen production ceases, 13.1 g of caprylic acid chloride, dissolved in 30 ml of tetrahydrofuran are added and the mixture is heated to 65°C for 3 hours. The solvent is evaporated under reduced pressure and the residue partitioned among water and ether. The hydrochloride is precipitated from the dried ether phase by passing HCl gas through the ether. Recrystallization of the product is effected from isopropanol. Yield, 11.7 g (47% of theory), M.P. 163° – 164°C.

EXAMPLE 4

[β-(4-Caprinyloxythymoxy)-ethyl]-dimethylamine

As in Example 3, 22.5 g of compound II are transformed to the sodium salt and reacted with 18.2 g of caprinic acid chloride, in tetrahydrofuran/dimethylsulfoxide (10:1). Time of heating is 1.5 hours at a temperature of 70°C. Further processing to obtain the product is as described above in Example 3. Yield, 27.4 g (64% of theory), M.P. 157° – 158°C (from N-butanol).

EXAMPLE 5

[β-(4-Isopropoxycarboxythymoxy)-ethyl]-dimethylamine

First, a suspension of 6.98 g of NaH (50%) in 100 cm³ dry tetrahydrofuran is prepared which is mixed dropwise with a solution of 34.4 g of compound II in 100 cm³ of tetrahydrofuran under cooling. Stirring is carried out at 60° – 70°C for 30 minutes following by cooling of the sodium compound solution. At 30° – 40°C a solution of 35 g of isopropyl chloroformate in a small amount of tetrahydrofuran is added dropwise followed by heating under reflux for 2 hours. Evaporation of the solvent is effected under reduced pressure and the residue taken up in diluted hydrochloric acid. After evaporation to dryness under reduced pressure the residue obtained is then taken up in 200 cm³ of boiling isopropanol which is then cooled and filtered. The filtrate is evaporated under reduced pressure and the oily residue crystallized with tetrahydrofuran. Yield, 20.8 g (from toluene), M.P. 180° – 181°C.

EXAMPLE 6

[β-(4-Isobutoxycarboxythymoxy)-ethyl]-dimethylamine

In an analogous manner as described in Example 5 by reaction of isobutylchloroformate in tetrahydrofuran there is obtained [β-(4-Isobutyoxycarboxythymoxy)-ethyl]-dimethylamine in a yield of 35%. The substance is melting at 172°C. (Oxalate)

EXAMPLE 7

[β-(4-Decanyl(2)-oxy-carboxythymoxy)-ethyl]-dimethylamine

In an analogous manner as described in Example 5 by reaction of 2-decanylchloroformate there is obtained [β-(4-decanyl(2)-oxy-carboxythymoxy)-ethyl]-dimethylamine in a yield of 30%. The substance is melting at 121.5°C. (Oxalate)

The utility of the present compound was compared, using recognized pharmaceutical tests, to that of thymoxamine, the group I compound of the prior art. The following pharmacological data are submitted:

Comparative studies between Thymoxamine (Substance A),
(4-Isopropoxycarboxy-thymyl)-(2'-dimethylaminoathyl)-ether.HCl (Compound 1),
(4-Caprinyloxy-thymyl)-(2'-dimethylaminoathyl)-ether.HCl (Compound 2) and
(4-Capryloxy-thymyl)-(2'-dimethylaminoathyl)-ether.HCl (Compound 3)

I. Acute Toxicity

The toxicity has been determined in a 7-day test with NMRI-mice having an average body weight of 18 to 26 g according to the method of Litchfield and Wilcoxon.

Table I

| Compound | LD 50 (mg/kg) | | | |
|---|---|---|---|---|
| | A | 1 | 2 | 3 |
| i.g. | 193.0 | 272.0 | 1020.0 | 400.0 |
| s.c | 156.0 | 210.0 | 1550.0 | — |
| i.v | 48.0 | 44.0 | 96.0 | 25.0 |

The compounds of the invention are in most of the cases less toxic than Thymoxamine (Compound A). S.c values of Compound 3 could not be established.

II. Effects on the peripheral flow a. Adrenaline stimulated nictitating-membrane of anesthetized cats This experiment is a classical model for the measurements of a peripheral vasodilation. Male and female cats have been anesthetized with pentobarbital. After tracheotomy the contraction of the nictitating-membrane was recorded by means of a strain-gauge. As stimulating agent 0.01 mg Adrenaline has been administered intravenously in intervals of 10 minutes. The results are reported in the following table II:

Table II

| Adrenaline stimulated nictitating-membrane | | | | |
|---|---|---|---|---|
| Compound mg/kg i.v. | A | 1 | 2 | 3 |
| 0.025 | 0 % | ~60 % | ~10 % | ~30 % |
| 0.5 | 0 % | 100 % | ~50 % | 80 % |
| 2 | 50 % | absolute inhibition no measurement possible | 80 % | 100 % |

Table II shows that Compounds 1, 2 and 3 are much more effective than Compound A.

b. Experiments on isolated rabbit ears

Male and female rabbits were killed 15 minutes after administration of heparine. Both ears were then cut off at the bases and examined according to Pissensky's method. The overflowing drops were measured by means of an electronic drop counter. The results are reported in table III.

Table III

| Increased number of drops measured in the isolated rabbit ear after administration of Compounds A, 1, 2 and 3 in %. | | | | |
|---|---|---|---|---|
| Compound | A | 1 | 2 | 3 |
| 0,025 mg | 14 % | ~10 % | 15 % | ~40 % |
| 0,5 mg | 15 % | ~20 % | 10 % | 80 % |
| 1 mg | 15 % | 34 % | 27 % | no more measurements possible |
| 2 mg | 16 % | 58 % | 68 % | |
| 4 mg | 16 % | 139 % | ~80 % | |

As can be seen from the table all tested compounds, especially No. 1, show an unexpected action on the vessels of isolated rabbit ears representative for an excellent peripheral vasodilation.

This data shows that the compounds of the present invention exhibit superior vasodilation and stability while having a higher lethal dose, i.e. greater safety, when compared to the commercially available compound.

We claim:

1. Compounds of the general formula I:

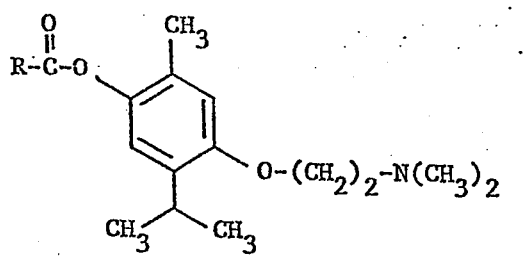

in which R represents an alkyl group of 8 to 11 carbon atoms or an alkoxy group R'—O— of 3 to 10 carbon atoms and the pharmaceutically acceptable salts thereof.

2. The compound of claim 1 which is [β-(4-Capryloxythymoxy)-ethyl]-dimethylamine.

3. The compound of claim 1 which is [β-(4-Caprinyloxythymoxy)-ethyl]-dimethylamine.

4. The compound of claim 1 which is [β-(4-Isopropoxycarboxythymoxy)-ethyl]-dimethylamine.

5. The compound of claim 1 which is [β-(4-Isobutoxycarboxythymoxy)-ethyl]-dimethylamine.

6. The compound of claim 1 which is [β-(4-Decanyl(2)-oxy-carboxythymoxy)-ethyl]-dimethylamine.

* * * * *